United States Patent
Al-Ali et al.

(10) Patent No.: US 7,500,950 B2
(45) Date of Patent: Mar. 10, 2009

(54) MULTIPURPOSE SENSOR PORT

(75) Inventors: Ammar Al-Ali, Tustin, CA (US);
Robert A Smith, Lake Forest, CA (US);
Rex J. McCarthy, Santa Ana, CA (US)

(73) Assignee: Masimo Corporation, Irvine, CA (US)

( * ) Notice: Subject to any disclaimer, the term of this patent is extended or adjusted under 35 U.S.C. 154(b) by 818 days.

(21) Appl. No.: 10/898,680

(22) Filed: Jul. 23, 2004

(65) Prior Publication Data

US 2005/0075548 A1    Apr. 7, 2005

Related U.S. Application Data

(60) Provisional application No. 60/490,091, filed on Jul. 25, 2003.

(51) Int. Cl.
*A61B 5/145* (2006.01)
(52) U.S. Cl. .................. 600/300; 600/322; 600/323
(58) Field of Classification Search ............. 600/300, 600/323, 322; 702/189
See application file for complete search history.

(56) References Cited

U.S. PATENT DOCUMENTS

| | | | |
|---|---|---|---|
| 4,960,128 A | 10/1990 | Gordon et al. | |
| 5,058,588 A * | 10/1991 | Kaestle | 600/323 |
| 5,163,438 A | 11/1992 | Gordon et al. | |
| 5,337,744 A | 8/1994 | Branigan | |
| 5,431,170 A | 7/1995 | Mathews | |
| 5,452,717 A | 9/1995 | Branigan et al. | |
| 5,482,036 A | 1/1996 | Diab et al. | |
| 5,490,505 A | 2/1996 | Diab et al. | |
| 5,494,043 A | 2/1996 | O'Sullivan et al. | |
| 5,533,511 A | 7/1996 | Kaspari et al. | |
| 5,590,649 A | 1/1997 | Caro et al. | |
| 5,632,272 A | 5/1997 | Diab et al. | |
| 5,638,816 A | 6/1997 | Kiani-Azarbayjany et al. | |
| 5,638,818 A | 6/1997 | Diab et al. | |
| 5,645,440 A | 7/1997 | Tobler et al. | |
| 5,685,299 A | 11/1997 | Diab et al. | |
| D393,830 S | 4/1998 | Tobler et al. | |
| 5,743,262 A | 4/1998 | Lepper, Jr. et al. | |
| 5,758,644 A | 6/1998 | Diab et al. | |
| 5,760,910 A | 6/1998 | Lepper, Jr. et al. | |
| 5,769,785 A | 6/1998 | Diab et al. | |
| 5,782,757 A | 7/1998 | Diab et al. | |
| 5,785,659 A | 7/1998 | Caro et al. | |
| 5,791,347 A | 8/1998 | Flaherty et al. | |
| 5,810,734 A | 9/1998 | Caro et al. | |
| 5,823,950 A | 10/1998 | Diab et al. | |
| 5,830,131 A | 11/1998 | Caro et al. | |
| 5,833,618 A | 11/1998 | Caro et al. | |

(Continued)

FOREIGN PATENT DOCUMENTS

EP    1 281 353 A1    2/2003

*Primary Examiner*—Eric F Winakur
*Assistant Examiner*—Etsub D Berhanu
(74) *Attorney, Agent, or Firm*—Knobbe Martens Olson & Bear, LLP.

(57) ABSTRACT

A sensor port is adapted to connect to either a sensor or a data source. A reader is configured to identify which of the sensor and the data source is connected to the sensor port. A data path is configured to communicate an analog signal associated with the sensor and digital data associated with the data source to a signal processor according to the identification made by the reader.

13 Claims, 10 Drawing Sheets

U.S. PATENT DOCUMENTS

| | | | |
|---|---|---|---|
| 5,860,919 A | 1/1999 | Kiani-Azarbayjany et al. | |
| 5,890,929 A | 4/1999 | Mills et al. | |
| 5,904,654 A | 5/1999 | Wohltmann et al. | |
| 5,919,134 A | 7/1999 | Diab | |
| 5,934,925 A | 8/1999 | Tobler et al. | |
| 5,940,182 A | 8/1999 | Lepper, Jr. et al. | |
| 5,995,855 A | 11/1999 | Kiani et al. | |
| 5,997,343 A | 12/1999 | Mills et al. | |
| 6,002,952 A | 12/1999 | Diab et al. | |
| 6,011,986 A | 1/2000 | Diab et al. | |
| 6,027,452 A | 2/2000 | Flaherty et al. | |
| 6,036,642 A | 3/2000 | Diab et al. | |
| 6,045,509 A | 4/2000 | Caro et al. | |
| 6,067,462 A | 5/2000 | Diab et al. | |
| 6,074,345 A * | 6/2000 | van Oostrom et al. | 600/300 |
| 6,081,735 A | 6/2000 | Diab et al. | |
| 6,088,607 A | 7/2000 | Diab et al. | |
| 6,110,522 A | 8/2000 | Lepper, Jr. et al. | |
| 6,151,516 A | 11/2000 | Kiani-Azarbayjany et al. | |
| 6,152,754 A | 11/2000 | Gerhardt et al. | |
| 6,157,850 A | 12/2000 | Diab et al. | |
| 6,165,005 A | 12/2000 | Mills et al. | |
| 6,184,521 B1 | 2/2001 | Coffin, IV et al. | |
| 6,206,830 B1 | 3/2001 | Diab et al. | |
| 6,229,856 B1 | 5/2001 | Diab et al. | |
| 6,236,872 B1 | 5/2001 | Diab et al. | |
| 6,256,523 B1 | 7/2001 | Diab et al. | |
| 6,263,222 B1 | 7/2001 | Diab et al. | |
| 6,278,522 B1 | 8/2001 | Lepper, Jr. et al. | |
| 6,280,213 B1 | 8/2001 | Tobler et al. | |
| 6,285,896 B1 | 9/2001 | Tobler et al. | |
| 6,334,065 B1 | 12/2001 | Al-Ali et al. | |
| 6,349,228 B1 | 2/2002 | Kiani et al. | |
| 6,360,114 B1 | 3/2002 | Diab et al. | |
| 6,371,921 B1 | 4/2002 | Caro et al. | |
| 6,377,829 B1 | 4/2002 | Al-Ali | |
| 6,388,240 B2 | 5/2002 | Schulz et al. | |
| 6,397,091 B2 | 5/2002 | Diab et al. | |
| 6,430,525 B1 | 8/2002 | Weber et al. | |
| 6,463,311 B1 | 10/2002 | Diab | |
| 6,470,199 B1 | 10/2002 | Kopotic et al. | |
| 6,501,975 B2 | 12/2002 | Diab et al. | |
| 6,515,273 B2 | 2/2003 | Al-Ali | |
| 6,525,386 B1 | 2/2003 | Mills et al. | |
| 6,526,300 B1 | 2/2003 | Kiani et al. | |
| 6,541,756 B2 | 4/2003 | Schulz et al. | |
| 6,542,764 B1 | 4/2003 | Al-Ali et al. | |
| 6,580,086 B1 | 6/2003 | Schulz et al. | |
| 6,584,336 B1 | 6/2003 | Ali et al. | |
| 6,597,933 B2 | 7/2003 | Kiani et al. | |
| 6,606,511 B1 | 8/2003 | Ali et al. | |
| 6,632,181 B2 | 10/2003 | Flaherty et al. | |
| 6,640,116 B2 | 10/2003 | Diab | |
| 6,643,530 B2 | 11/2003 | Diab et al. | |
| 6,650,917 B2 | 11/2003 | Diab et al. | |
| 6,654,624 B2 | 11/2003 | Diab et al. | |
| 6,658,276 B2 | 12/2003 | Kianl et al. | |
| 6,671,531 B2 | 12/2003 | Al-Ali et al. | |
| 6,678,543 B2 | 1/2004 | Diab et al. | |
| 6,684,090 B2 | 1/2004 | Ali et al. | |
| 6,697,656 B1 | 2/2004 | Al-Ali | |
| 6,697,658 B2 | 2/2004 | Al-Ali | |
| RE38,476 E | 3/2004 | Diab et al. | |
| 6,699,194 B1 | 3/2004 | Diab et al. | |
| 6,714,804 B2 | 3/2004 | Al-Ali et al. | |
| RE38,492 E | 4/2004 | Diab et al. | |
| 6,725,075 B2 | 4/2004 | Al-Ali | |
| 6,745,060 B2 | 6/2004 | Diab et al. | |
| 6,760,607 B2 | 7/2004 | Al-All | |
| 2002/0062070 A1 | 5/2002 | Tschupp et al. | |
| 2003/0088165 A1* | 5/2003 | Smith et al. | 600/323 |
| 2004/0260154 A1* | 12/2004 | Sidelnik et al. | 600/300 |

* cited by examiner

MULTIPURPOSE SENSOR PORT

REFERENCE TO RELATED APPLICATIONS

The present application claims benefit of U.S. Provisional Application No. 60/490,091 filed Jul. 25, 2003, entitled "Multipurpose Sensor Port." The present application incorporates the disclosure of the foregoing application herein by reference.

BACKGROUND OF THE INVENTION

A pulse oximeter is a physiological instrument that provides noninvasive measurements of arterial oxygen saturation along with pulse rate. To make these measurements, a pulse oximeter performs a spectral analysis of the pulsatile component of arterial blood so as to determine the relative concentration of oxygenated hemoglobin, the major oxygen carrying constituent of blood. Pulse oximeters provide early detection of decreases in the arterial oxygen supply, reducing the risk of accidental death and injury. As a result, these instruments have gained rapid acceptance in a wide variety of medical applications, including surgical wards, intensive care units, general wards and home care.

Figure 1:
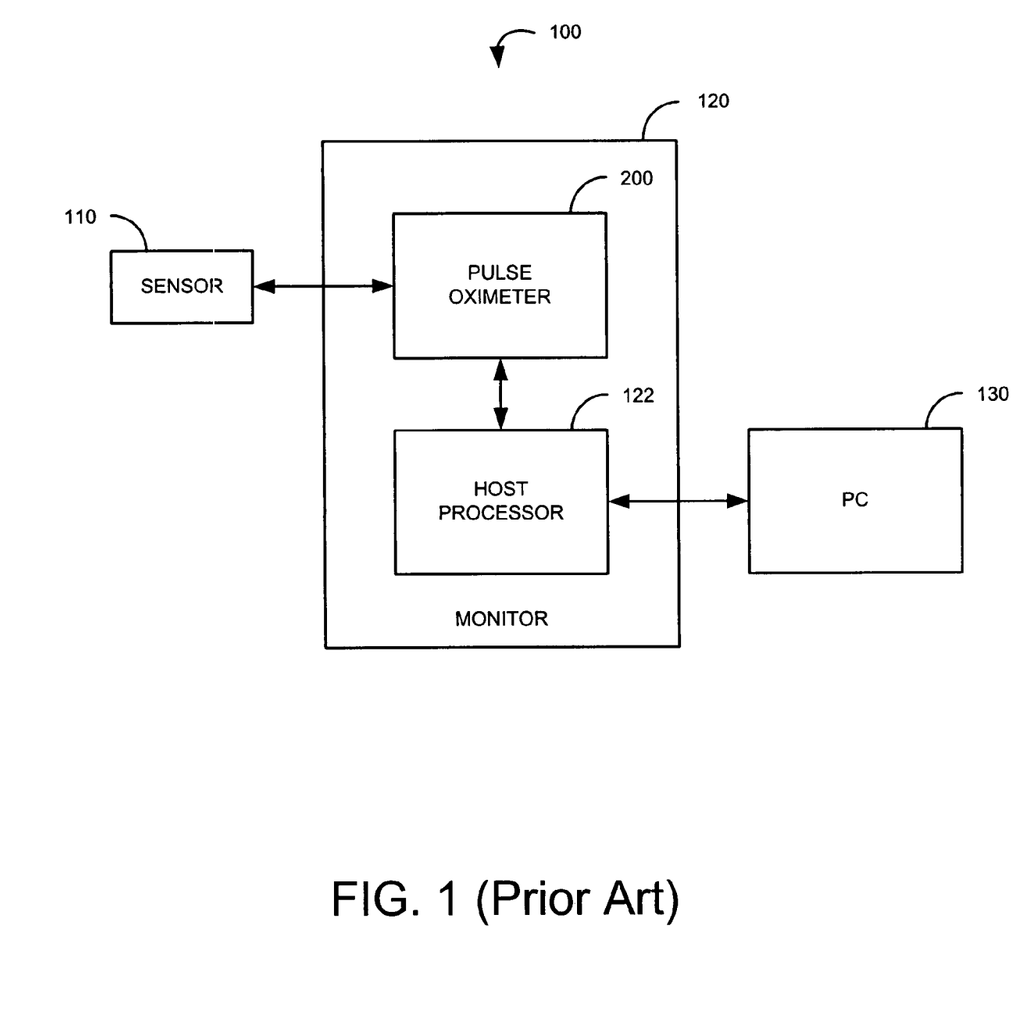
FIG. 1 is a general block diagram of a prior art pulse oximeter system utilizing an OEM printed circuit board (PCB)

FIG. 1 illustrates a pulse oximetry system 100 having a sensor 110 and a monitor 120. The monitor 120 may be a multi-parameter patient monitor or a standalone, portable or handheld pulse oximeter. Further, the monitor 120 may be a pulse oximeter 200, such as an OEM printed circuit board (PCB), integrated with a host instrument including a host processor 122, as shown. The sensor 110 attaches to a patient and receives drive current from, and provides physiological signals to, the pulse oximeter 200. An external computer (PC) 130 may be used to communicate with the pulse oximeter 200 via the host processor 122. In particular, the PC 130 can be used to download firmware updates to the pulse oximeter 200 via the host processor 122, as described below.

Figure 2:
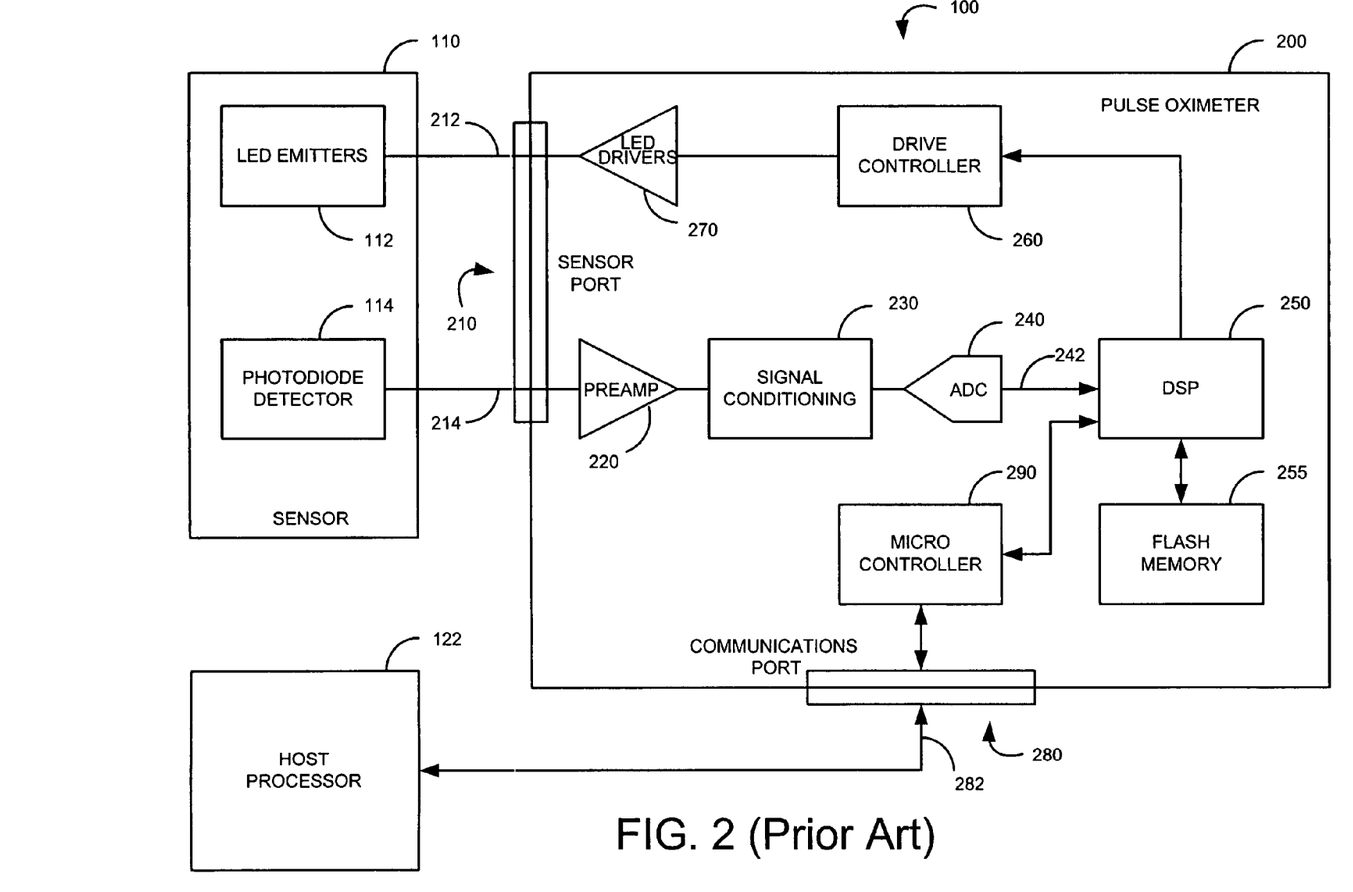
FIG. 2 is a detailed block diagram of a prior art pulse oximeter system.

FIG. 2 illustrates further detail of the pulse oximetry system 100. The sensor 110 has emitters 112 and a detector 114. The emitters 112 typically consist of a red light emitting diode (LED) and an infrared LED that project light through blood vessels and capillaries underneath a tissue site, such as a fingernail bed. The detector 114 is typically a photodiode positioned opposite the LEDs so as to detect the emitted light as it emerges from the tissue site. A pulse oximetry sensor is described in U.S. Pat. No. 6,088,607 entitled "Low Noise Optical Probe," which is assigned to Masimo Corporation, Irvine, Calif. and incorporated by reference herein.

As shown in FIG. 2, the pulse oximeter 200 has a preamp 220, signal conditioning 230, an analog-to-digital converter (ADC) 240, a digital signal processor (DSP) 250, a drive controller 260 and LED drivers 270. The drivers 270 alternately activate the emitters 112 as determined by the controller 260. The preamp 220, signal conditioning 230 and ADC 240 provide an analog front-end that amplifies, filters and digitizes the current generated by the detector 114, which is proportional to the intensity of the light detected after tissue absorption in response to the emitters 112. The DSP 250 inputs the digitized, conditioned detector signal 242 and determines oxygen saturation, which is based upon the differential absorption by arterial blood of the two wavelengths projected by the emitters 112. Specifically, a ratio of detected red and infrared intensities is calculated by the DSP 250, and arterial oxygen saturation values are empirically determined based upon the ratio obtained. Oxygen saturation and calculated pulse rate values are communicated to the host processor 122 for display by the monitor 120 (FIG. 1). A pulse oximeter is described in U.S. Pat. No. 6,236,872 entitled "Signal Processing Apparatus," which is assigned to Masimo Corporation, Irvine, Calif. and incorporated by reference herein.

Further shown in FIG. 2, the pulse oximeter 200 has a sensor port 210 and a communications port 280. The sensor port 210 includes a connector and associated input and output signals and provides an analog connection to the sensor 110. In particular, the sensor port 210 transmits a drive signal 212 to the LED emitters 112 from the LED drivers 270 and receives a physiological signal 214 from the photodiode detector 114 in response to the LED emitters 112, as described above. The communication port 280 also includes a connector and associated input and output signals and provides a bi-directional communication path 282 between the pulse oximeter 200 and the host processor 122. The communication path 282 allows the DSP 250 to transmit oxygen saturation and pulse rate values to the monitor 120 (FIG. 1), as described above. The communication path 282 also allows the DSP firmware to be updated, as described below.

Additionally shown in FIG. 2, the pulse oximeter 200 has a micro-controller 290 and a flash memory 255. The flash memory 255 holds the stored program or firmware that executes on the DSP 250 to compute oxygen saturation and pulse rate. The micro-controller 290 controls data transfers between the DSP 250 and the host processor 122. In particular, to update the DSP firmware, the firmware is uploaded into the PC 130 (FIG. 1), which downloads the firmware to the host processor 122. In turn, the host processor 122 downloads the firmware to the micro-controller 290, which downloads it to the DSP 250. Finally, the DSP 250 writes the firmware to the flash memory 255.

SUMMARY OF THE INVENTION

To update the firmware in a pulse oximeter, particularly firmware on an OEM PCB integrated into a host instrument, requires a circuitous path using multiple protocols and multiple processors developed by different companies. Some of the protocols and processor interfaces are non-standard, requiring custom programming for different instruments. This is particularly problematic when the instruments are part of an installed base at various medical facilities. Further, some pulse oximeter products, such as handheld products, may not have a communications port for connecting to an external computer, and firmware upgrades would typically require returning the instrument to the factory.

Every pulse oximeter has a sensor port, which provides access to a DSP via one or more signal paths. Therefore, it is desirable to utilize a sensor port for downloading pulse oximetry firmware to the DSP. It is also desirable to provide this sensor port capability in existing instruments without hardware modification. Utilizing a sensor port in this manner would alleviate an instrument manufacturer from having to provide download communication capability between a host processor and an OEM PCB and would allow easy field upgrades of all instruments, including handhelds.

One aspect of a multipurpose sensor port is a physiological measurement method comprising a sensor port adapted to connect with an analog sensor, and a digital data source connected to the sensor port. An identifier associated with said data source is read, where the identifier is indicative that the data source is connected to the sensor port in lieu of the analog sensor. Digital data is then received over the sensor port. In one embodiment, the digital data is compiled in a signal processor. Where the digital data are instructions executable by the signal processor, the data may then be written from the signal processor into a firmware memory. The instructions may be uploaded to a PC, which is attached to a PC interface that is attached to the sensor port. Alternatively, the instructions are stored into a nonvolatile memory that is in communications with the sensor port. In another embodiment, the digital data is processed as a physiological signal.

Another aspect of a multipurpose sensor port is a physiological measurement system having a sensor port adapted to connect to a sensor and a data source. A reader is configured to identify which of the sensor and the data source is connected to the sensor port. A data path is configured to communicate an analog signal associated with the sensor and digital data associated with the data source to a signal processor according to the reader. In one embodiment, a firmware memory is configured to provide instructions to the signal processor. The signal processor is programmed to download the instructions from the data source and store the instructions in the memory. The instructions are executable by the signal processor so as to extract a physiological measurement from the analog signal. The data source may be a PC interfaced to the sensor port, where the instructions are uploaded to the PC. Alternatively, the data source is a nonvolatile memory adapted to communicate with the sensor port, where the instructions being stored in a nonvolatile memory.

In another embodiment, a first physiological measurement is derivable by the signal processor from the analog signal, and a second physiological measurement is derivable by the signal processor from the digital data. In yet another embodiment, a drive path is configured to communicate stored data associated with a physiological measurement to a digital device connected to the sensor port. The stored data may be trend data and/or log data maintained in memory that can be accessed by the signal processor. In a further embodiment, a drive path is configured to communicate acknowledgement data in conjunction with the communication of the digital data.

Yet another aspect of a multipurpose sensor port is a physiological measurement method where a drive path is provided that is adapted to activate emitters so as to transmit optical radiation through a fleshy medium having flowing blood. A signal path is provided that is adapted to communicate a detector response to the optical radiation after attenuation by the fleshy medium, where the response is indicative of optical characteristics of the flowing blood. Output digital data is transmitted over at least a portion of the drive path. In one embodiment, the output digital data is read from a memory having trend data and/or log data. In another embodiment, input digital data is received over at least a portion of the signal path, and receipt of that input digital data is acknowledged with the output digital data. In a particular embodiment, the input digital data is stored for use as signal processing instructions.

DETAILED DESCRIPTION OF THE PREFERRED EMBODIMENT

Overview

Figure 3A:
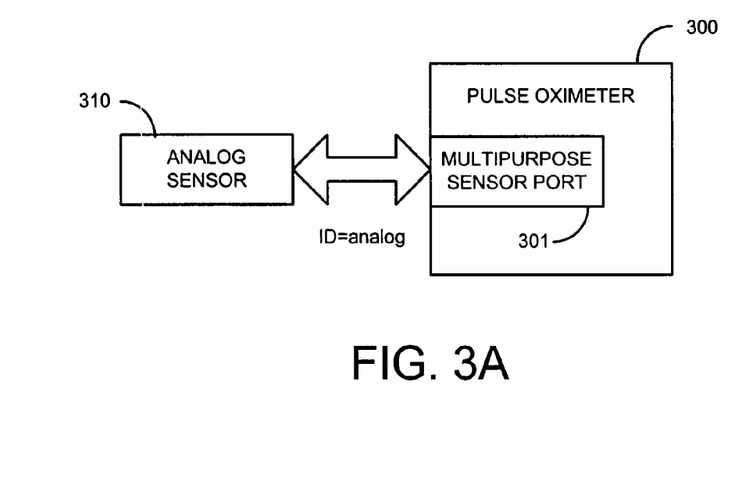
FIGS. 3A-D are general block diagrams of a multipurpose sensor port connected to an analog sensor, a digital data source, or both.
Figure 3B:
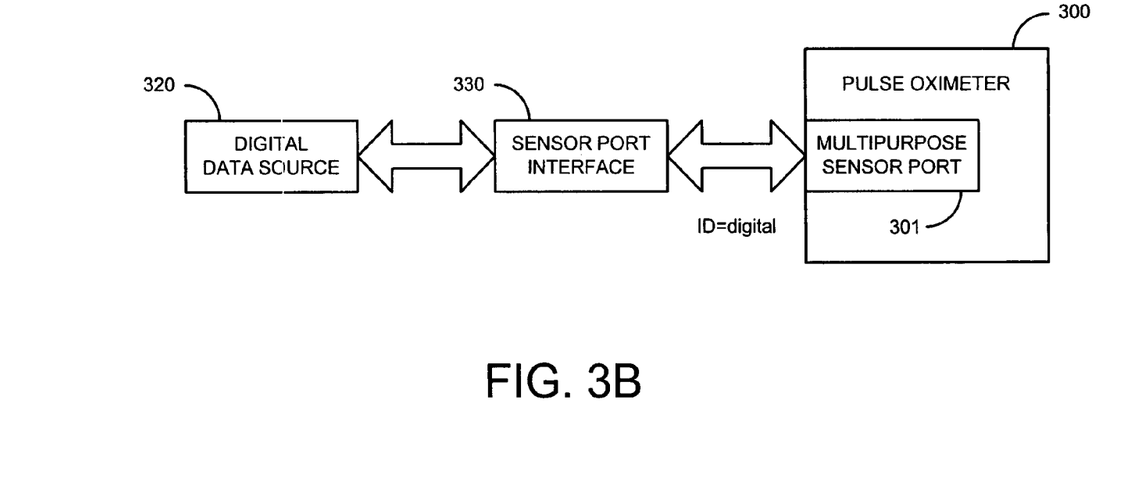

FIGS. 3A-B illustrate a pulse oximeter 300 having a multipurpose sensor port 301 connected to an analog sensor 310 and a digital data source 320, respectively. As shown in FIG. 3A, if the pulse oximeter 300 determines that an analog sensor 310 is attached to the multipurpose sensor port 301, the multipurpose sensor port 301 is operated in an analog mode and functions as a typical sensor port, described above. As shown in FIG. 3B, if the pulse oximeter 300 determines that a digital data source 320 is attached to the multipurpose sensor port 301, the multipurpose sensor port 301 is operated in a digital mode and functions as a digital communications device. The data source 320 may connect to a sensor port interface 330 which, in turn, connects to the sensor port 301. The sensor port interface 330 may be used, for example, to present a standard communications interface, such as RS-232, to the data source 320. In one embodiment, when the pulse oximeter 300 is powered up, it reads an information element or other means of identification (ID) for the device connected to the sensor port 301. The ID identifies the device as either an analog sensor 310 or a data source 320. A sensor information element is described in U.S. Pat. No. 6,397,091 entitled "Manual and Automatic Probe Calibration," which is assigned to Masimo Corporation, Irvine, Calif. and incorporated by reference herein.

Figure 3C:
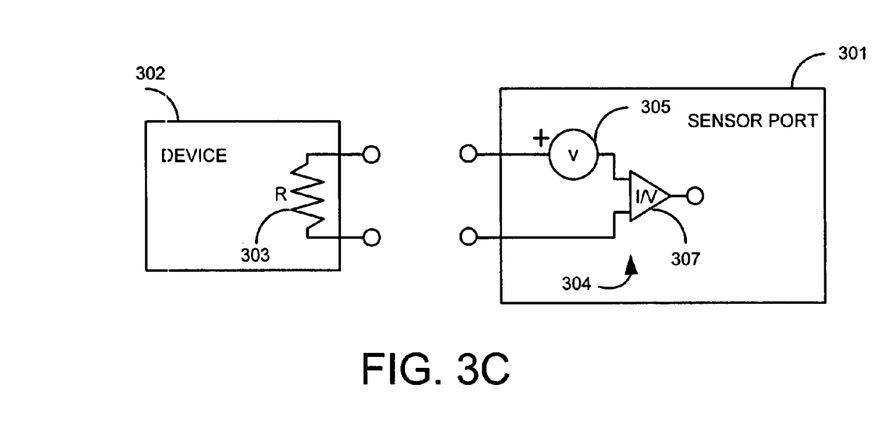

FIG. 3C illustrates a sensor port embodiment where a resistor value is a device ID. A resistor 303 is located in a device 302, which includes a sensor 310 (FIG. 3A), data source 320 (FIG. 3B) or interface 330 (FIG. 3B). The sensor port 301 has a reader 304 that measures the resistor value. The reader 304 includes a voltage source 305 and a current measurement device 307, such as a current-to-voltage converter. The voltage source 305 has a known voltage, which is applied to the resistor 303 when the device 302 is connected to the sensor port 301. The current measurement device 307 senses the magnitude of the resulting current flowing through the resistor 303 so as to determine the resistor value and, hence, the device ID.

Figure 3D:
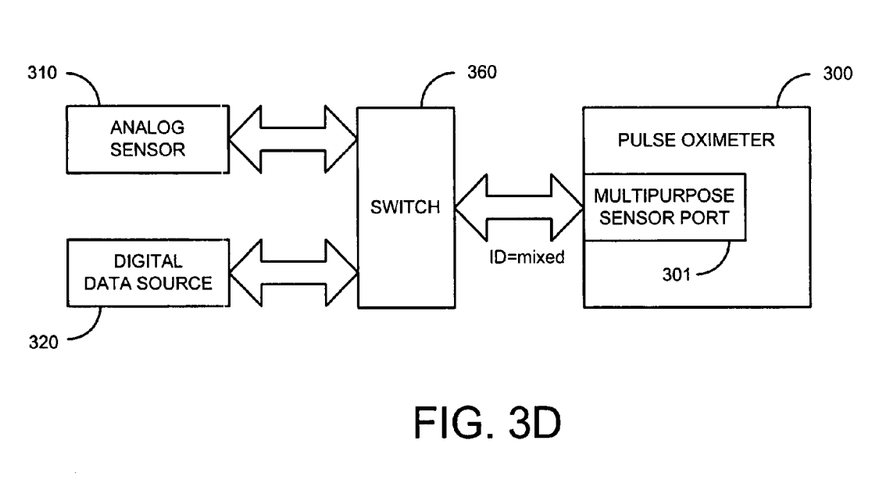

FIG. 3D illustrates a pulse oximeter 300 having an analog sensor 310, a digital data source 320 and a switch 360 connected to a multipurpose sensor port 301. If the pulse oximeter 300 reads an ID that identifies mixed analog and digital, then the multipurpose sensor port 301 functions to transfer either an analog signal or digital data, as determined by the switch 360. The state of the switch 360 may be determined by the data source 320, the pulse oximeter 300 or both. In one embodiment, the pulse oximeter 300 transmits an identifiable waveform over an LED drive path 510 (FIG. 5) that is recognized by the switch 360 as a change state command. In this manner, the pulse oximeter 300 may occasionally receive digital data from, or transmit digital data to, the data source 320.

Applications

Figure 4:
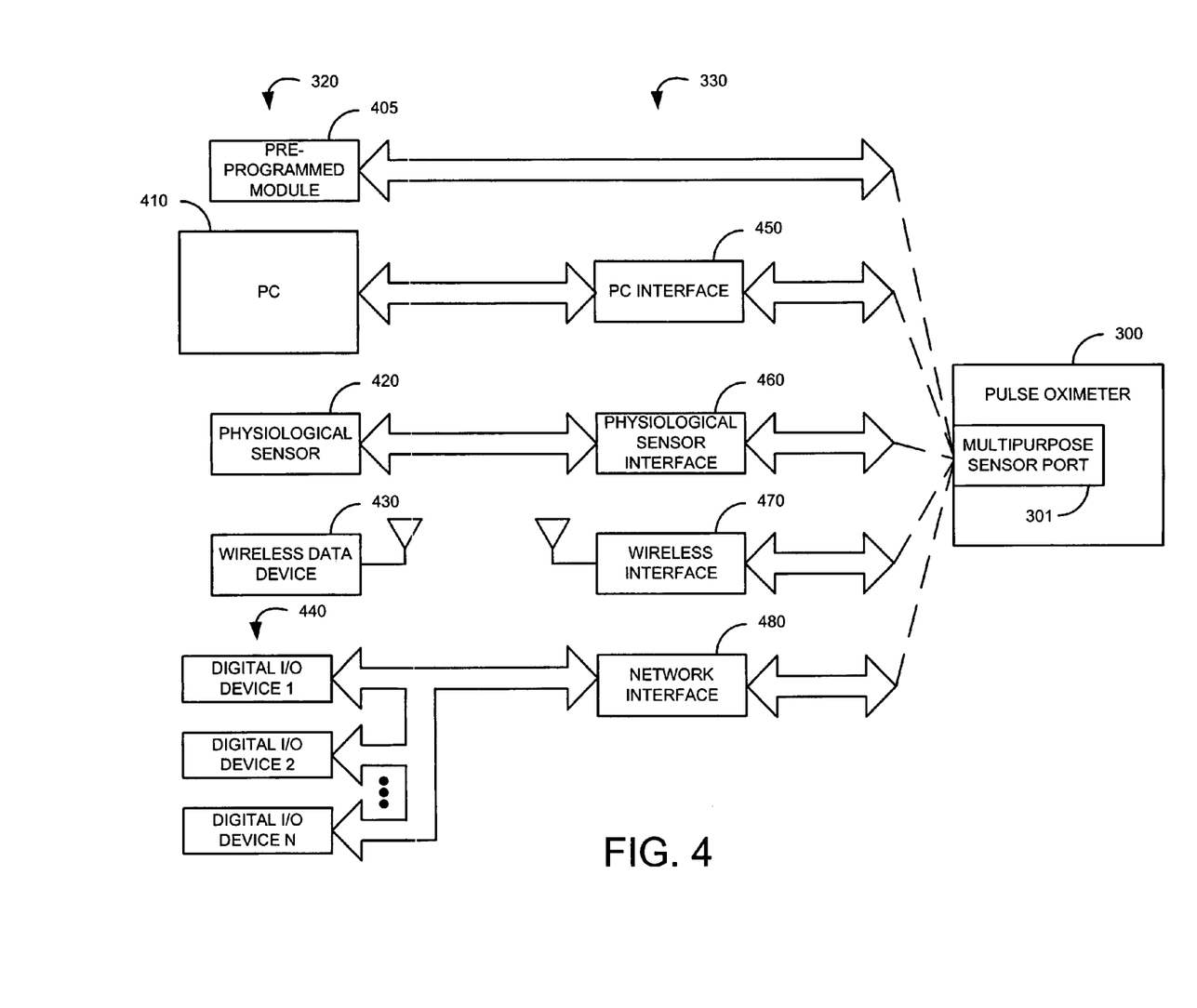
FIG. 4 is a general block diagram of a multipurpose sensor port having various digital data source inputs.

FIG. 4 illustrates various digital data source 320 and sensor port interfaces 330 that connect to a multipurpose sensor port 301. In one application, a preprogrammed module 405 connects directly to the sensor port 301. The module 405 has nonvolatile memory preprogrammed with, for example, upgrade firmware for the pulse oximeter 300. The module 405 also has the associated electronics to readout the memory data and communicate that data to the sensor port 301. In particular, the module 405 provides mechanical, signal level, and communication protocol compliance with the sensor port 301.

As shown in FIG. 4, in another application, a PC 410 connects to the sensor port 301 via a PC interface 450. For example, the PC 410 can be used to download firmware to the pulse oximeter 300, as described with respect to FIG. 5, below. As another example, the PC 410 can be used to upload information from the pulse oximeter 300, as described with respect to FIG. 6, below. In one embodiment, the PC interface 450 provides mechanical and signal level compliance with RS-232 on the PC side and mechanical and signal level compliance with the sensor port 301 on the pulse oximeter side, as described with respect to FIG. 9, below.

Also shown in FIG. 4, a physiological sensor 420 other than a conventional pulse oximeter sensor is attached to the multipurpose sensor port 301. A physiological sensor interface 460 drives the physiological sensor 420 and generates raw digital data to the sensor port 301. In this manner, a pulse oximeter 300 can be advantageously extended to provide physiological measurements in addition to oxygen saturation and pulse rate.

Further shown in FIG. 4, a wireless data device 430 is attached to the multipurpose sensor port 301 via a wireless interface 470. In this manner, the pulse oximeter can be advantageously extended to wireless data I/O and wireless networks. In one embodiment, the wireless interface 470 provides mechanical and signal level compliance with a wireless standard, such as IEEE-802.11, on one side and mechanical and signal level compliance with the sensor port 301 on the pulse oximeter side.

Additionally shown in FIG. 4, networked digital I/O devices 440 are attached to the multipurpose sensor port 301 via a network interface 480. In one embodiment, the network interface 480 provides mechanical and signal level compliance with a network standard, such as Ethernet, on one side and mechanical and signal level compliance with the sensor port 301 on the pulse oximeter side.

Firmware Upgrade Port

Figure 5:
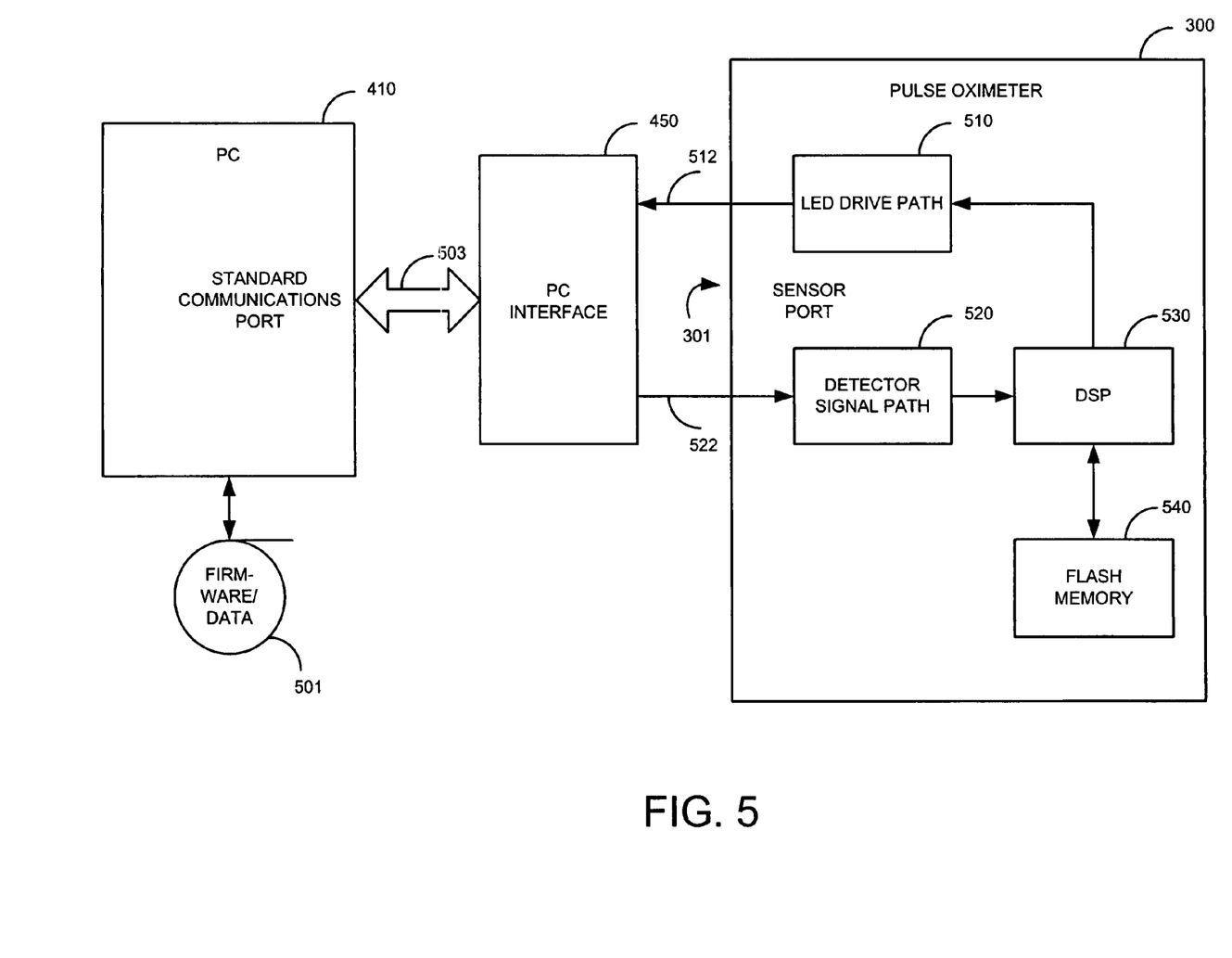
FIG. 5 is a block diagram of a multipurpose sensor port configured to download pulse oximeter firmware.

FIG. 5 illustrates a multipurpose sensor port 301 configured to download pulse oximeter firmware 501. The firmware 501 is uploaded to a PC 410 and downloaded over a standard communications bus 503 to a target pulse oximeter 300. The standard bus 503 may be, for example, RS-232, IEEE-488, SCSI, IEEE-1394 (FireWire), and USB, to name just a few. A PC interface 450 translates the signal levels on the sensor port 301 to the signal levels of the standard bus 503, and vice-a-versa. In particular, an output signal on the standard bus 503 is translated to a sensor port input signal 522, and a sensor port output signal 512 is translated to an input signal on the standard bus 503.

As shown in FIG. 5, the pulse oximeter 300 has a detector signal path 520, a DSP 530, a flash memory 540 or other nonvolatile memory and a LED drive path 510, such as described with respect to FIG. 2, above. Data transmitted from the PC 410 is carried on the sensor port input 522, over the detector signal path 520 to the DSP 530, which loads the data into a flash memory 540. Acknowledgement data is transmitted from the DSP 530, over the LED drive path 510, and is carried on the sensor port output 512.

Figure 6:
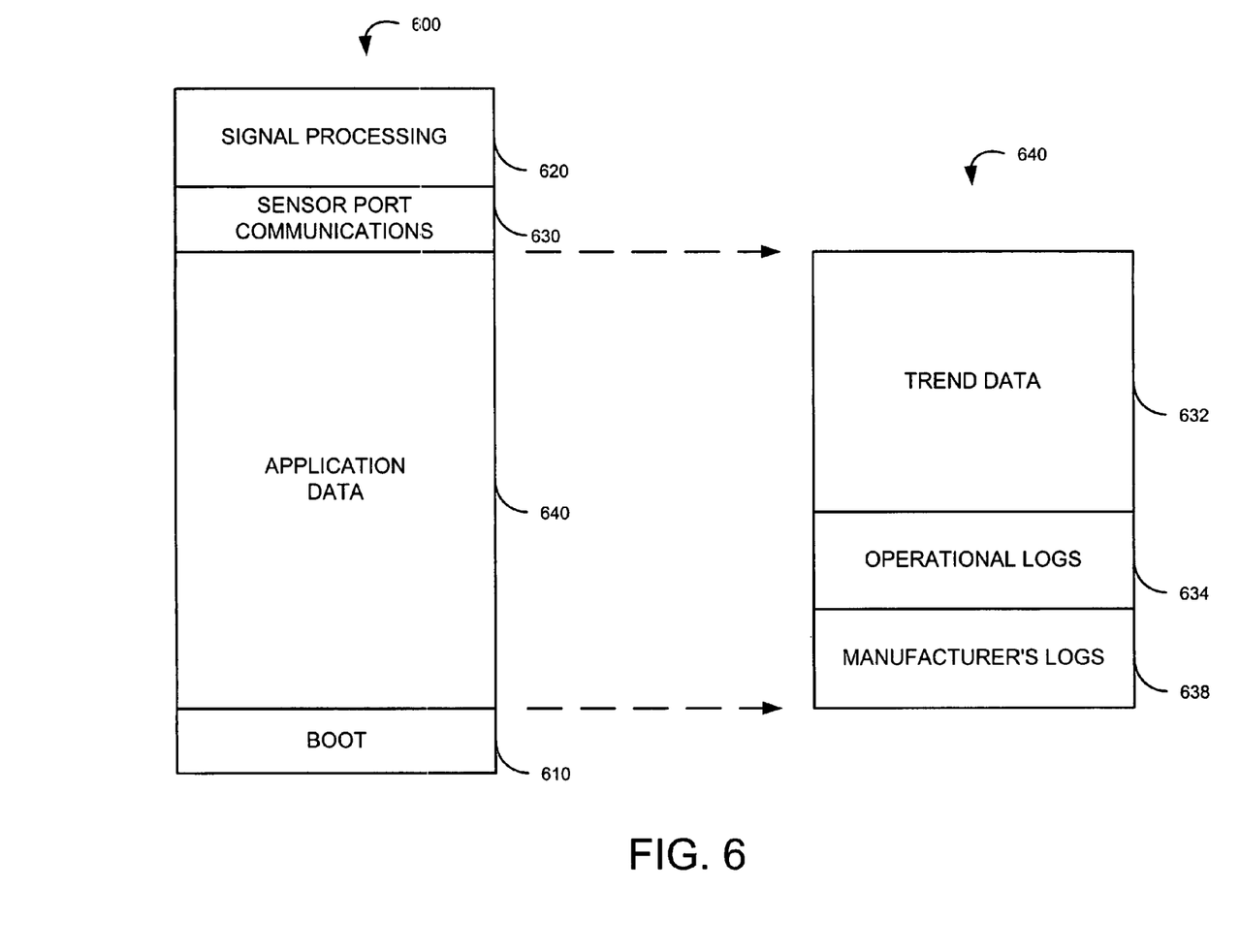
FIG. 6 is a DSP firmware memory map.

FIG. 6 illustrates a memory map 600 for the DSP flash memory 540 (FIG. 5). The memory map 600 illustrates partitions for DSP executable instructions such as boot firmware 610, signal processing firmware 620 and sensor port communications firmware 630 in addition to application data 640. The boot firmware 610 executes upon DSP power-up. The boot firmware 610 initializes the DSP and loads either the signal processing firmware 620 or the communications firmware 630 into DSP program memory, depending on the device ID, as described with respect to FIGS. 3A-D, above. The signal processing firmware 620 contains the oxygen saturation and pulse rate measurement algorithms, referred to with respect to FIGS. 1-2, above. The communications firmware 630 contains communications protocol algorithms, such as described with respect to FIG. 8, below. After completing its task of downloading firmware and/or uploading the applications data 640, the communications firmware 630 loads the signal processing firmware 620 so that the DSP can perform pulse oximetry measurements.

Also shown in FIG. 6, the application data 640 includes trend data 632, operational logs 634 and manufacturer's logs 638, which can be advantageously uploaded to a PC 410 (FIG. 5) or other digital device connected to the sensor port 301 (FIG. 5). Trend data 632 contains oxygen saturation and pulse rate measurement history. Operational logs 634 contain, for example, failure codes and event information. Failure codes indicate, for example, pulse oximeter board failures and host failures. Event information includes alarm data, such as the occurrence of probe off and low saturation events. Manufacturer's logs 638 contains, for example, service information.

Figure 7:
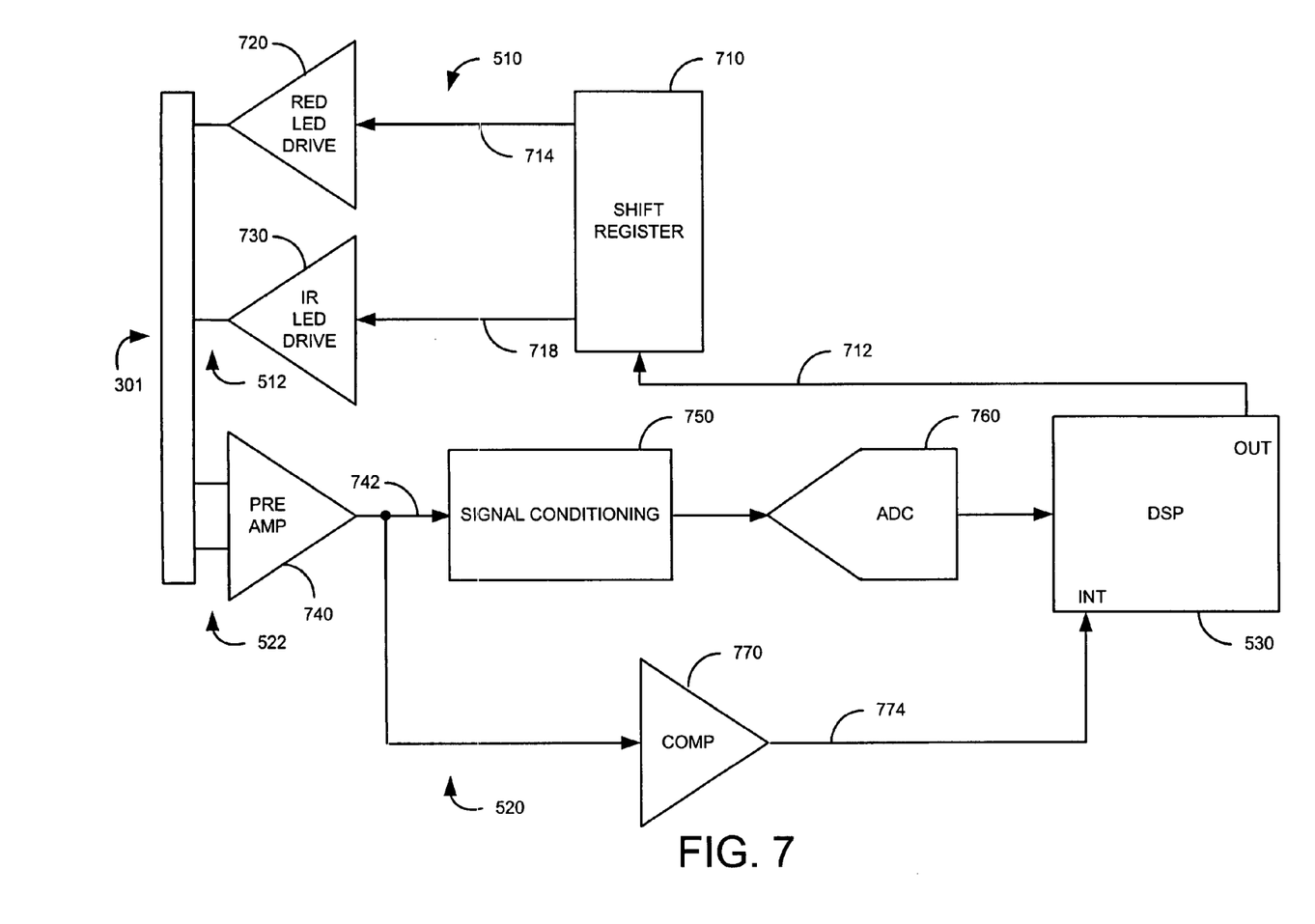
FIG. 7 is a detailed block diagram of a multipurpose sensor port embodiment and associated signal and data paths.

FIG. 7 illustrates a multipurpose sensor port embodiment 301 incorporating an LED drive path 510, a detector signal path 520 and a DSP 530, which function generally as described with respect to FIG. 5, above. The LED drive path 510 has a shift register 710, a red LED drive 720 and an IR LED drive 730. The shift register 710 has a data input 712, a red control output 714 and an IR control output 718. The DSP 530 provides serial control data on the shift register input 712 that is latched to the shift register outputs 714, 718 so as to turn on and off the LED drives 720, 730 according to a predetermined sequence of red on, IR on and dark periods. The detector signal path 520 has a preamp 740, signal conditioning 750 and an ADC 760 that perform amplification, filtering and digitization of the detector signal 522. The detector signal path 520 also has a comparator 770 that compares the preamp output 742 to a fixed voltage level and provides an interrupt output 774 to the DSP 530 accordingly. The comparator 770 allows the DSP to control the preamp voltage as a function of the level of the preamp signal output 742, as described in U.S. patent application Ser. No. 10/351,961 entitled "Power Supply Rail Controller," filed Jan. 24, 2003, which is assigned to Masimo Corporation, Irvine, Calif. and incorporated by reference herein. Advantageously, the comparator signal path also allows the DSP to accept serial digital data, as described with respect to FIG. 8, below.

Figure 8:
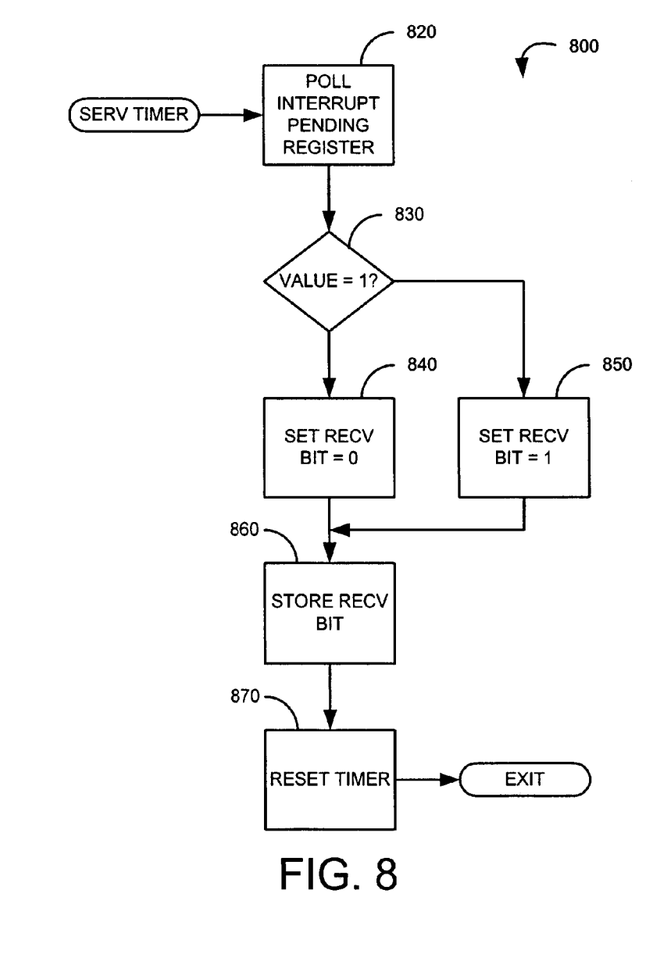
FIG. 8 is a flowchart of a digital data receiver routine.

FIG. 8 illustrates a serial data receiver 800 embodiment of one aspect of the communications firmware 630 (FIG. 6). The data receiver 800 utilizes the detector signal path 520 (FIG. 7) described above. A DSP internal timer is initialized to generate an interrupt at the incoming data baud rate. The timer interrupt periodically starts the data receiver 800 to determine and store a single bit. The data receiver 800 polls the status of the DSP interrupt input 774 (FIG. 7), which is initialized to be level-sensitive and disabled. Thus, whenever the comparator 770 (FIG. 7) is triggered, it will latch into a DSP interrupt pending register but will not generate an interrupt event. The timer service routine 800 polls the interrupt pending register 820. The pending register value is determined 830. If the value is a "1," then a zero bit has been received 840, else a one bit has been received 850. The received bit is stored 860 and the timer reset 870.

Figure 9:
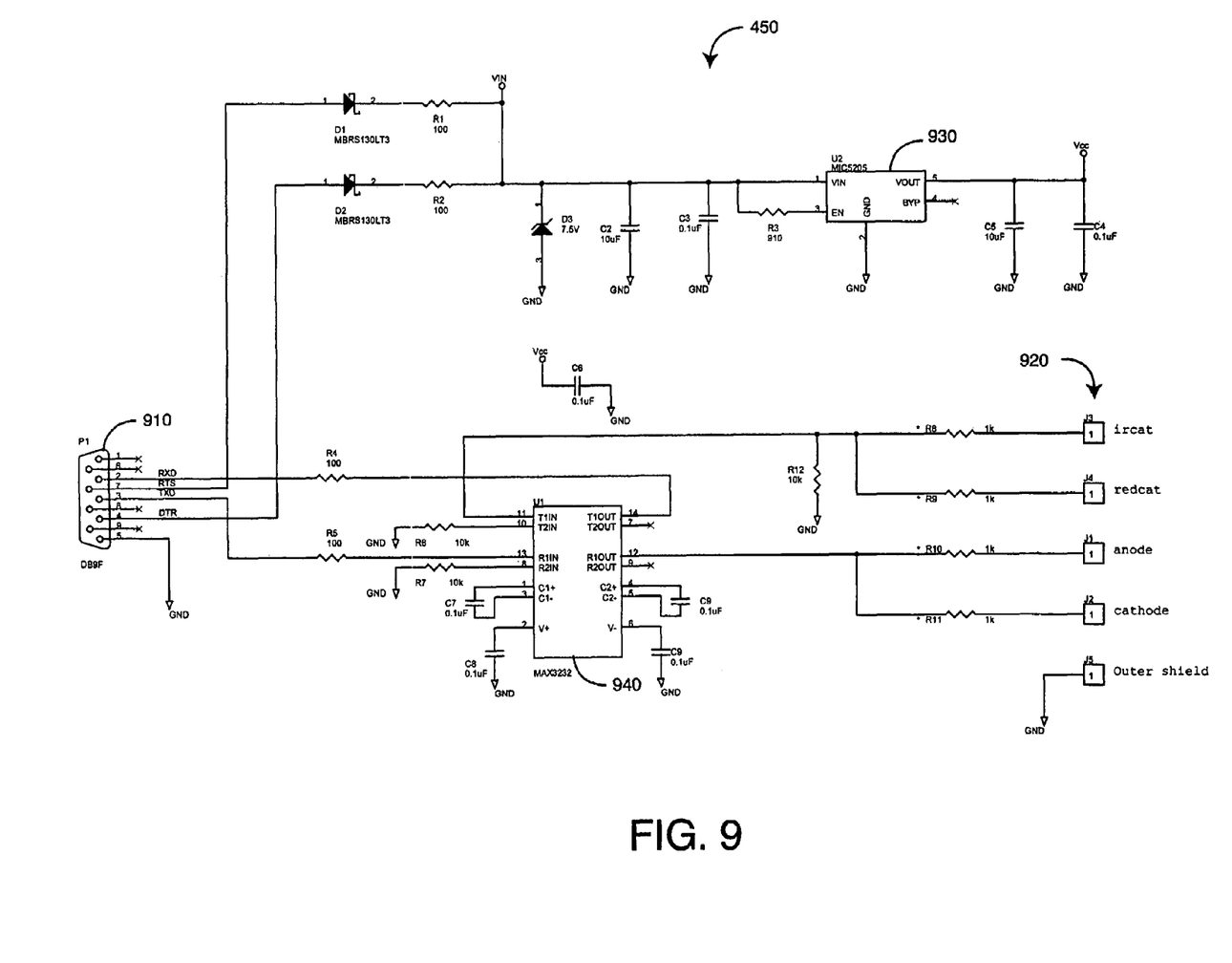
FIG. 9 is a schematic of a RS232 interface for a multipurpose sensor port.

FIG. 9 illustrates an RS-232 PC interface embodiment 450 having an RS-232 connector 910, a sensor connector 920, a voltage regulator 930 and a transceiver 940. The voltage regulator 930 draws power from either the RS-232 910 RTS (request to send) or DTR (data terminal ready) signal lines and provides regulated VCC power to transceiver 940. The transceiver 940 operates on either of the sensor 920 red or IR drive signal lines to generate an RS-232 910 RXD (receive data) signal. The transceiver 940 further operates on the RS-232 TXD (transmit data) signal line to generate a sensor 920 detector signal.

A multipurpose sensor port has been disclosed in detail in connection with various embodiments. These embodiments are disclosed by way of examples only and are not to limit the scope of the claims that follow. One of ordinary skill in the art will appreciate many variations and modifications.

What is claimed is:

1. A method of operating a dual-use coupling for a patient monitor, the method comprising:

providing a drive path adapted to activate emitters so as to transmit optical radiation through a fleshy medium having flowing blood, said drive path including conductors of a mechanical coupling of a physiological monitor, said coupling adapted to mechanically mate with cabling in communication with a noninvasive physiological sensor;

providing a signal path adapted to communicate a detector response to said optical radiation after attenuation by said fleshy medium, said response indicative of optical characteristics of said flowing blood, said signal path including conductors of said mechanical coupling, said emitters and said detector forming at least a portion of said sensor; and transmitting digital data from devices other than components of said noninvasive physiological sensor over at least a portion of said drive path at said mechanical coupling.

2. The method according to claim 1 comprising the further step of reading said digital data from a memory of said monitor, said memory having at least one of trend data and log data.

3. The method according to claim 1 comprising the further step of receiving digital data from devices other than components of said noninvasive physiological sensor over at least a portion of said signal path at said mechanical coupling.

4. The method according to claim 3 comprising the further step of storing said digital data for use as signal processing instructions.

5. A method of operating a patient monitor to noninvasively monitor one or more physiological parameters of a patient and to receive non-physiological measurement digital data, the method comprising the steps of:

providing a sensor port adapted to connect with a noninvasive sensor including emitters and a detector adapted to detect light from said emitters after attenuation by tissue at a tissue site of said patient, said sensor port adapted to alternatively connect with a digital data source to receive at least non-physiological measurement digital data, wherein only one of said sensor or said digital data source can be connected with said sensor port at a time;

when said sensor is connected with said sensor port, receiving through said sensor port a detector signal from said detector and processing said detector signal to determine said one or more physiological parameters; and when said digital data source is connected with said sensor port in the place of said sensor, reading an identifier associated with said data source, said identifier indicative that said data source is connected to said sensor port, and receiving through said sensor port said non-physiological measurement digital data.

6. The method according to claim 5 comprising accessing said digital data with a signal processor.

7. The method according to claim 6 comprising writing said digital data from said signal processor into a firmware memory, said digital data comprising a plurality of instructions executable by said signal processor.

8. The method according to claim 7 wherein said data source comprises a PC.

9. The method according to claim 7 comprising:

storing said instructions into a nonvolatile memory; and
   providing communications between said nonvolatile memory and said sensor port.

10. A physiological measurement system adapted for communication with computing devices through a connector generally associated with receipt of measurement signals, the system comprising:

a signal processor configured to receive one or more signals from a noninvasive sensor responsive to a detector signal indicative of noninvasively detected light attenuated by body tissue of a patient, the processor also configured to process said one or more signals to determine one or more physiological parameters of said patient, the processor also configured to communicate with a data source storing non-physiological related data;

a sensor port including a single connection adapted to communicate with said sensor and adapted to communicate with said data source, at least a portion of conductors communicating with said sensor when said sensor is connected being used to communicate with said data source when said data source is connected;

a reader configured to identify which of said sensor and said data source is connected to said sensor port; and a data path configured to communicate said one or more signals associated with said sensor and digital data associated with said data source to said signal processor according to said reader.

11. The physiological measurement system according to claim 10 comprising:

a firmware memory configured to provide instructions to said signal processor, said signal processor programmed to download said instructions from said data source and store said instructions in said memory, said instructions executable by said signal processor so as to extract a physiological measurement from said one or more received signals.

12. The physiological measurement system according to claim 11 wherein said data source comprises a PC interfaced to said sensor port, said instructions being uploaded to said PC.

13. The physiological measurement system according to claim 11 wherein said data source is a nonvolatile memory adapted to communicate with said sensor port, said instructions being stored in a nonvolatile memory.

* * * * *